US007850591B2

(12) United States Patent  (10) Patent No.: US 7,850,591 B2
Spector  (45) Date of Patent: Dec. 14, 2010

(54) MAGNETIC THERAPEUTIC WAND, APPARATUS AND METHOD

(76) Inventor: Donald Spector, 641 Fifth Ave., New York, NY (US) 10022

( * ) Notice: Subject to any disclaimer, the term of this patent is extended or adjusted under 35 U.S.C. 154(b) by 1223 days.

(21) Appl. No.: 11/355,331

(22) Filed: Feb. 16, 2006

(65) Prior Publication Data

US 2007/0191670 A1  Aug. 16, 2007

Related U.S. Application Data

(60) Provisional application No. 60/771,078, filed on Feb. 6, 2006.

(51) Int. Cl.
*A61M 37/00* (2006.01)
(52) U.S. Cl. ...................................................... 600/12
(58) Field of Classification Search ............... 600/9–15; 128/897, 899; 604/890–892
See application file for complete search history.

(56) References Cited

U.S. PATENT DOCUMENTS

| | | | |
|---|---|---|---|
| 4,162,672 A | | 7/1979 | Yazaki |
| 4,683,461 A | * | 7/1987 | Torre ........................... 340/551 |
| 4,798,194 A | | 1/1989 | Amishima |
| 4,951,675 A | * | 8/1990 | Groman et al. ............. 424/9.32 |
| 5,123,898 A | * | 6/1992 | Liboff et al. .................. 600/13 |
| 5,128,644 A | * | 7/1992 | Nellessen .................... 335/306 |
| 5,162,037 A | | 11/1992 | Whitson-Fischman |
| 5,518,495 A | * | 5/1996 | Kolt ............................. 600/13 |
| 5,782,743 A | | 7/1998 | Russell |
| 5,921,244 A | * | 7/1999 | Chen et al. ................... 128/897 |
| 5,928,227 A | * | 7/1999 | Howard et al. ................ 606/40 |
| 6,001,055 A | | 12/1999 | Souder |
| 6,050,931 A | | 4/2000 | Russell |
| 6,074,385 A | * | 6/2000 | Klopotek ....................... 606/27 |
| 6,085,751 A | * | 7/2000 | Taparia ........................ 128/897 |
| 6,231,497 B1 | | 5/2001 | Souder |
| 6,304,080 B1 | * | 10/2001 | Reznik et al. .......... 324/207.25 |
| 6,328,685 B1 | | 12/2001 | Korsgaard |
| 6,358,196 B1 | * | 3/2002 | Rayman ....................... 600/12 |
| 6,961,620 B2 | * | 11/2005 | Rioux et al. ................... 607/99 |
| 7,419,468 B2 | * | 9/2008 | Shimizu et al. ............. 600/117 |
| 2004/0138663 A1 | * | 7/2004 | Kosashvili et al. ............ 606/62 |

OTHER PUBLICATIONS

RCO Sales, Inc. "Benchtop Gaussmeters." Dec. 24, 2008. <http://www.rcosales.com/fwbenchtop.asp>.*

* cited by examiner

*Primary Examiner*—Samuel G Gilbert
(74) *Attorney, Agent, or Firm*—Sunstein Kann Murphy & Timbers LLP

(57) ABSTRACT

Methods and apparatus to magnetize particles and objects either on the surface of the skin or inside the body are disclosed. Methods and apparatus for measuring the magnet field strength emanated by an object are also disclosed. The object may be in a body, such as a surgically implanted device. The object may also be cream externally applied to skin, the cream containing particles that can be magnetized. The object may also be a pill that can be swallowed.

25 Claims, 9 Drawing Sheets

MAGNETIC THERAPEUTIC WAND, APPARATUS AND METHOD

CROSS-REFERENCE TO RELATED APPLICATIONS

This application claims the benefit of U.S. Provisional Application No. 60/771,078, filed Feb. 6, 2006, which is incorporated herein by reference.

BACKGROUND OF THE INVENTION

Exposure of organs, bones and tissue to static magnetic fields provides relief to patients suffering pain. A number of articles have addressed the therapeutic qualities associated with magnetic fields. A number of products have been designed, most of which do not work well. They do not work well, in part, because they do not apply a magnetic field directly to the area that needs treatment.

New and improved methods and apparatus to apply magnetic fields to objects to obtain a therapeutically beneficial result are required.

SUMMARY OF THE INVENTION

In accordance with one aspect of the present invention, a device that is a magnetizer is presented. The magnetizer, in accordance with another aspect of the present invention includes a meter. This will disclose, with some degree of accuracy, the magnetic charge that it has emitted to either internal screws, orthopedic devices or micro encapsulated ferrous substances. This meter is easy to use and inexpensive, however since magnetic materials discharge over time it is important to be able to measure, control and replace the fading magnetic charge as needed. The meter is used in conjunction with the magnetic field system, but does not necessarily have to be connected, since the patient may wish to monitor the field at home. Thus, the meter and the magnetizer can be provided in kit form. The magnetizer can be used on micro encapsulated skin cream that includes magnetic particles. The magnetism can also be used to increase the charges of metallic, ferrous or other magnetizable object already inside the body.

The method and apparatus of the present invention, preferably has the proper warning for people with pacemakers or other devices that might be sensitive to magnetic fields.

In accordance with a further aspect of the present invention, an apparatus for magnetizing materials for therapeutic purposes includes a magnetic field generator that generates a magnetic field and a meter that measures magnetic field strength. The apparatus preferably, but not necessarily, includes a switch that enables and disables the operation of the magnetic field generator. The switch can also enable and disable the meter, further preferably disabling the meter when the magnetic field generator is enabled and enabling the meter when the magnetic field generator is disabled. Alternatively, a second switch that enables and disables the meter can be provided.

In accordance with another aspect of the present invention, the meter can be enabled when the magnetic field generator is enabled to measure the magnetic field generated by the magnetic field generator.

A control that regulates the strength of the magnetic field can also be provided on the apparatus. A timer that enables the magnetic field generator for a selected time can also be provided on the apparatus.

In accordance with a further aspect of the present invention, the apparatus is used to apply a dosage of the magnetic field to an object in a human body so that the object generates a therapeutic magnetic field. The object can be any magnetizable object, including but not limited to orthopedic devices. Such orthopedic devices can include metallic screws and pins.

In accordance with another aspect of the present invention, the apparatus is used to apply a magnetic field to a pill so that the pill generates a therapeutic magnetic field. The pill can be, for example, a microencapsulated metallic material or a microencapsulated ferrous material. The pill also includes a therapeutic amount of a drug or other material. The apparatus is used to apply a magnetic field to the pill when the pill is outside a body, and then the pill is swallowed. The meter can be used to determine the magnetic field emanating from the pill before or after swallowing.

In accordance with a further aspect of the present invention, the meter measures the therapeutic magnetic field on the object. The meter can also be used to measure magnetic fields associated with different parts of a body.

The meter can include a display. The display indicates a strength of a magnetic field emanating from an object in a human body. In accordance with one aspect of the present invention, the display has an indication of whether the magnetic field is above or below a threshold. If the measured magnetic field is below a threshold, then the meter indicates by an alarm that the magnetic field generator should be used to apply a magnetic field to the object.

The present invention also contemplates a kit for magnetizing materials for therapeutic purposes. The kit includes at least two components, including a magnetic field generator that generates a magnetic field and a meter that measures magnetic field strength that is separate from the magnetic field generator.

The magnetic field generator and the meter can be used in the same manner previously described.

The present invention also contemplates a method of providing a therapeutic magnetic field. The method includes applying a dosage of magnetic field generated by a magnetic field generator to an object and measuring the magnetic field strength emanating from the object with a meter.

The strength of the applied magnetic field can be controlled by a controller or a timer. As previously described, the device can be an object inside a body or a pill.

The method can further include the step of applying a second dosage of magnetic field generated by the magnetic field generator if the magnetic field strength is less than a threshold.

In an alternative method, a meter can be used to measure the magnetic field emanating from an object before applying a magnetic field to the object. The magnetic field would be generated and applied to the object depending on the reading on the meter.

DESCRIPTION OF A PREFERRED EMBODIMENT

The present invention relates to the field of magnetic therapy. Many people experience beneficial effects (including a reduction in the feeling of pain) by having tissue, bones or organs being exposed to static magnetic fields. These fields are typically applied by magnets located outside the body.

In accordance with one aspect of the present invention, an apparatus including a magnetic field generator and a meter to provide dosages of therapeutic magnetic fields to patients is provided. In accordance with another aspect of the present invention, a kit that includes a magnetic field generator and a meter packaged together is provided. These devices are used to magnetize objects that are inside a body, on the skin of a body or to be swallowed by a body so that the objects can provide a magnetic field. The magnetic field will be of greater strength because the objects are inside the body and will be of greater benefit because they are near tissue, organs or bones that require therapy to assist in healing. The meter can be used to measure the magnetic field on the object to allow the application of appropriate dosages. The meter can also be used in accordance with another aspect of the present invention to measure the magnetic field output by the magnetic field generator to allow accurate measurement of the dose of magnetic field applied.

In many cases patients already have objects or materials in their bodies, on their bodies or that will be put inside their bodies that can be magnetized. Metal parts like screws, fixators, plates, prostheses are examples of metal parts and implants that may be present in a body.

Figure 1:
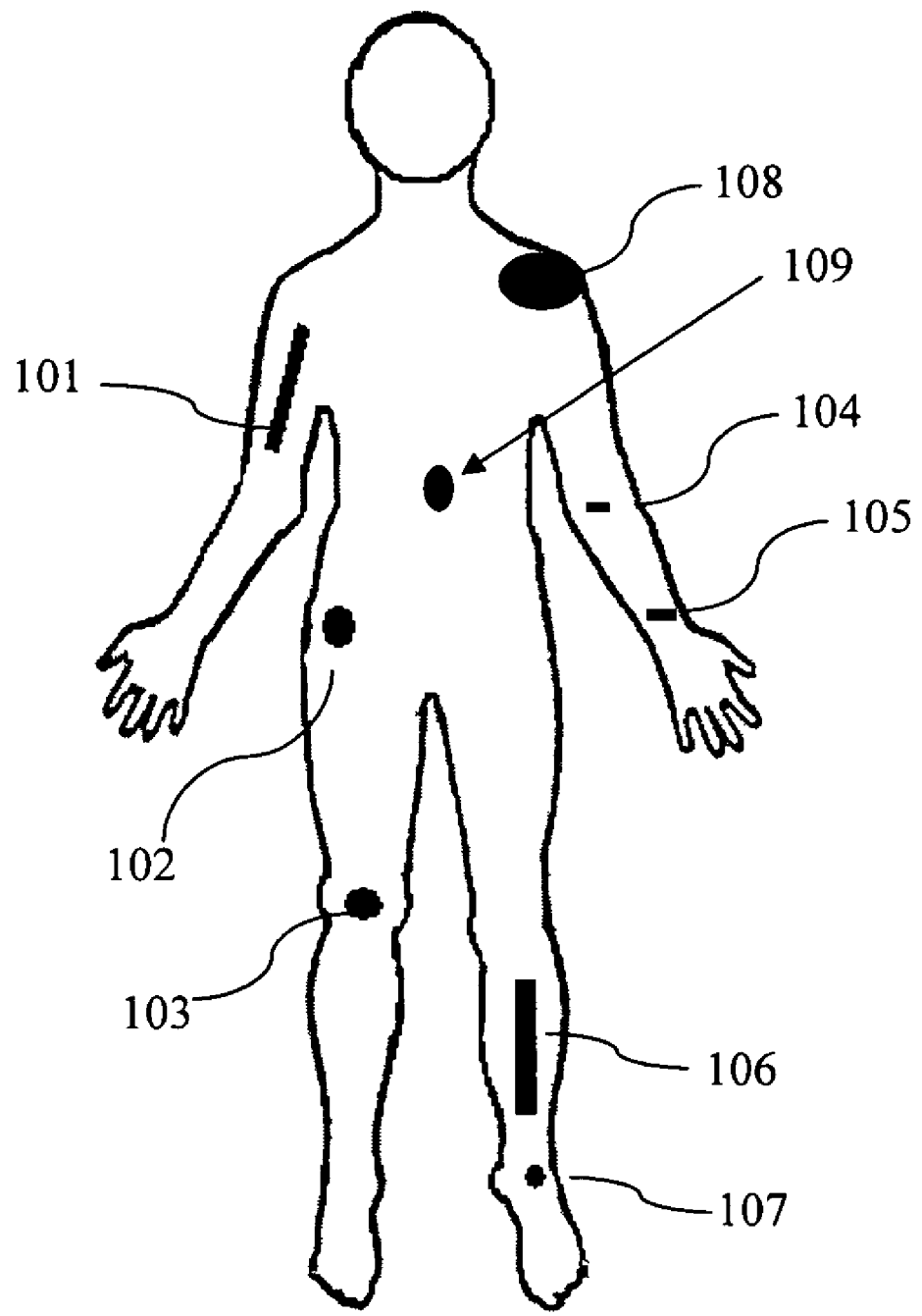
FIG. 1 provides a diagram of a human body with illustrative examples of locations of magnetizable objects.

This is shown in diagram in FIG. 1. FIG. 1 is a diagram of the human body with, for illustrative purposes only, locations where metal parts and implants are known to be applied. This includes areas and items such as humeral implants 101, hip implants 102, knee implants 103, elbow joint implants 104, screws for joint fixation 105, tibial component of knee replacement 106 and implants for ankle reconstruction 107.

Other components that can be magnetized are pills that include a therapeutic material and a magnetizable material. For example, the pills may be micro encapsulated metallic or ferrous substances. These substances can be ingested, or implanted in the body. Referring to FIG. 1, a pill is illustrated in the digestive system 109 of the body.

Creams or lotions that include magnetizable material, such as metals, that can be applied to the exterior of the body, such as the skin at location 108. The magnetic material in the creams or lotions can also be magnetized so that the creams or lotions emit a magnetic field. For example, the creams or lotions can include any metal, such as ferrous material.

In accordance with one aspect of the present invention, the apparatus or kit of the present invention, either with or without the meter, applies a magnetic field to any of the objects illustrated in FIG. 1 to magnetize the objects. The objects will therefore emit a magnetic field. This magnetic field will be close to tissue, organs or bones that will benefit from the therapeutic effects of a magnetic field.

In an initial state, the magnetizable materials or objects may contain no, or a very weak magnetic field. It is also known that over time magnetized materials may lose strength in their magnetic field. In accordance with one aspect of the present invention, the strength of a magnetic field applied to the objects of FIG. 1 is determined so that the strength of the magnetic field emanated by the objects is maintained at a level that will not be reduced below a minimal desired strength. It is also preferable to magnetize the objects within a body to a defined level. It is also preferred to repeat magnetization of objects at a certain time with the same magnetic field as at previous occasions.

The present invention addresses these needs for applying known and repeatable levels of magnetic field strengths. The device that is used for generating a magnetic field is a magnetic field generator. Magnetic Field Generators are well known. One aspect of the present invention is to provide a magnetic field generator as a therapeutic instrument that includes a meter to disclose the strength or the dosage of the magnetic field that is applied to the objects in the body.

Figure 2:
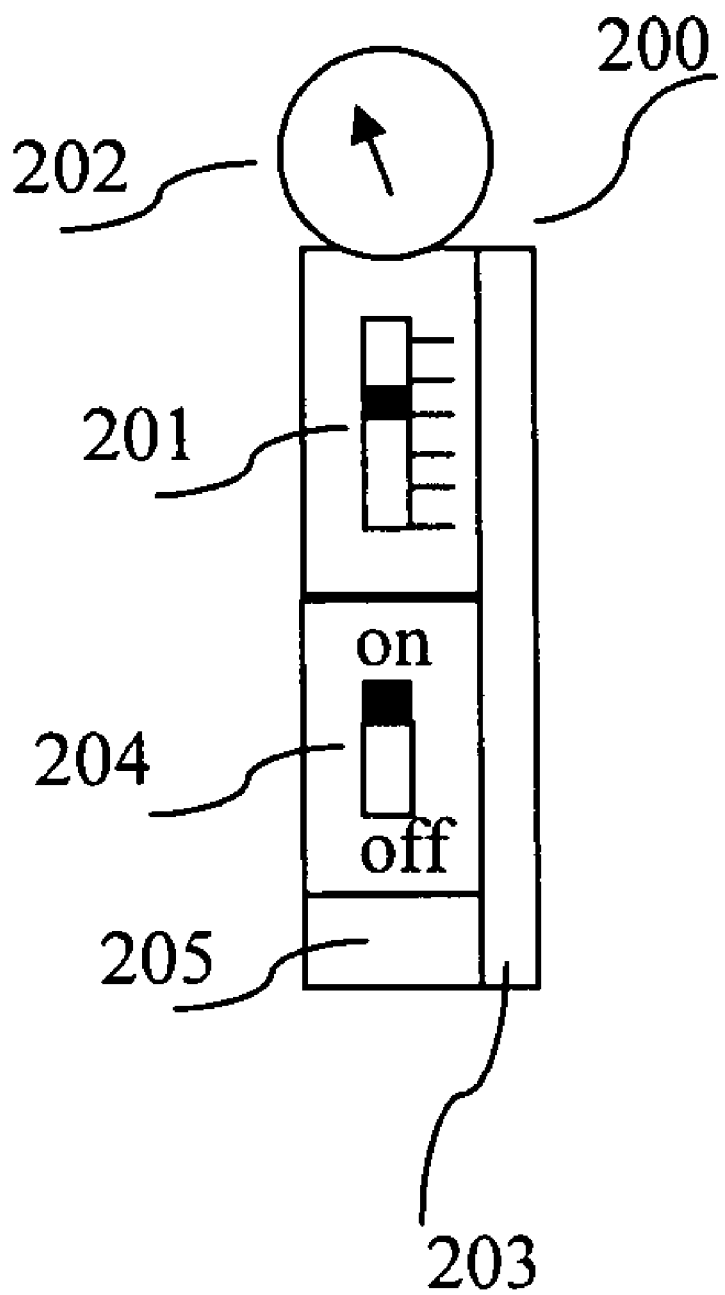
FIGS. 2 and 3 show magnetizing devices.

One embodiment of a therapeutic device in accordance with the present invention is shown in FIG. 2. The device can be fixed in a rigid package. In accordance with one preferred aspect of the present invention, the device is provided in a wand like construction and is completely mobile.

The magnetizing device 200 in FIG. 2 is comprised of the following components. It has a magnetic field generator 203 that generates a magnetic field. There are different known ways to generate a magnetic field, of which one is by electrically energized coils. The magnetizing device 200 also has a regulator 201. This regulator 201 allows the strength of the generated magnetic field to be controlled. In the case of an electrical magnetizer, the regulator may be a potentiometer that regulates the strength of the current to the coils and thus can regulate the strength of the magnetic field. The regulator 201 has different setting positions, which can be indicated by a scale. The magnetizer also comprises an on/off switch 204. The on/off switch enables and disables the generation of a magnetic field by the magnetic field generator 203 as desired. In accordance with a further aspect of the present invention, the magnetizing device 200 includes a meter 202. This meter can provide an indication of the strength of the generated magnetic field in the direct neighborhood of the magnetizer 200. Consequently this specific magnetizer provides a method to generate a therapeutic magnetic field of known strength. And it can be used at different times, after having been used at different settings in a desired setting generating a magnetic field of known strength. In case the magnetizer is an electrical magnetizer, a power source 205 is provided.

The meter 202 can also be used to measure the magnetic field emanating from an object that has been magnetized. For example, the magnetic field strength emanating from any of the objects of FIG. 1. can be measured using the meter 202, however, the magnetic field generator 203 should be disabled when taking the measurement. Thus, in one embodiment of the present invention, the switch 204 enables the generator 203 and disables the meter 202 in one position and enables the meter 202 and disables the generator 203 in another position.

Figure 3:
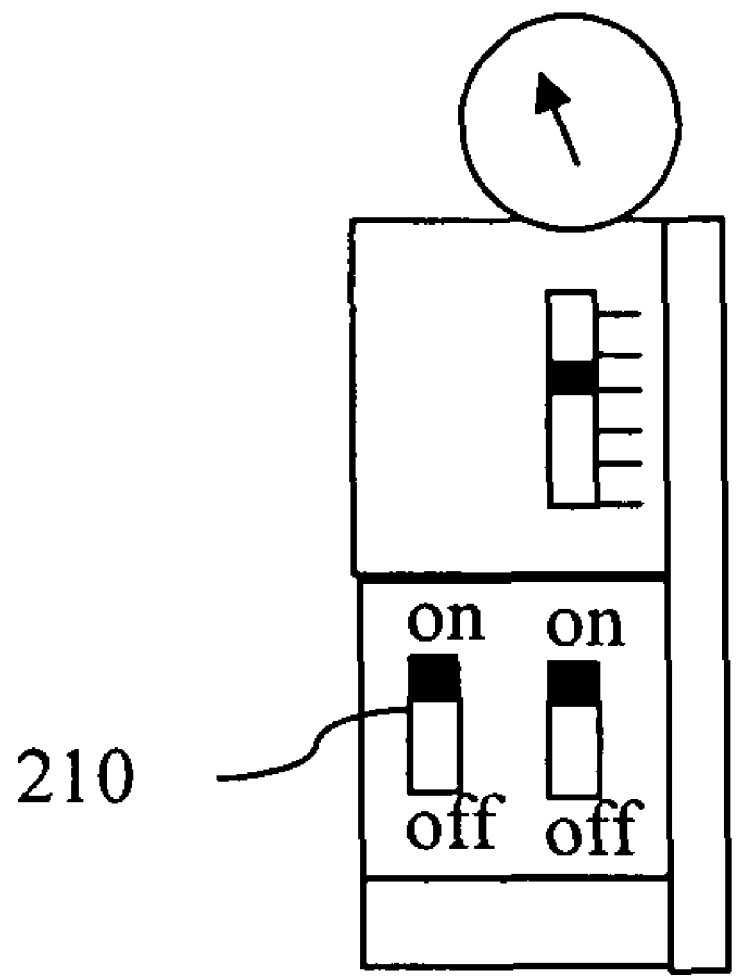

FIG. 3 illustrates another embodiment of the present invention. In FIG. 3, the magnetizing device includes a second on/off switch 210. The first switch is used to control the magnetic field generator 203 and the switch 210 is used to control the meter 202.

Figure 4:
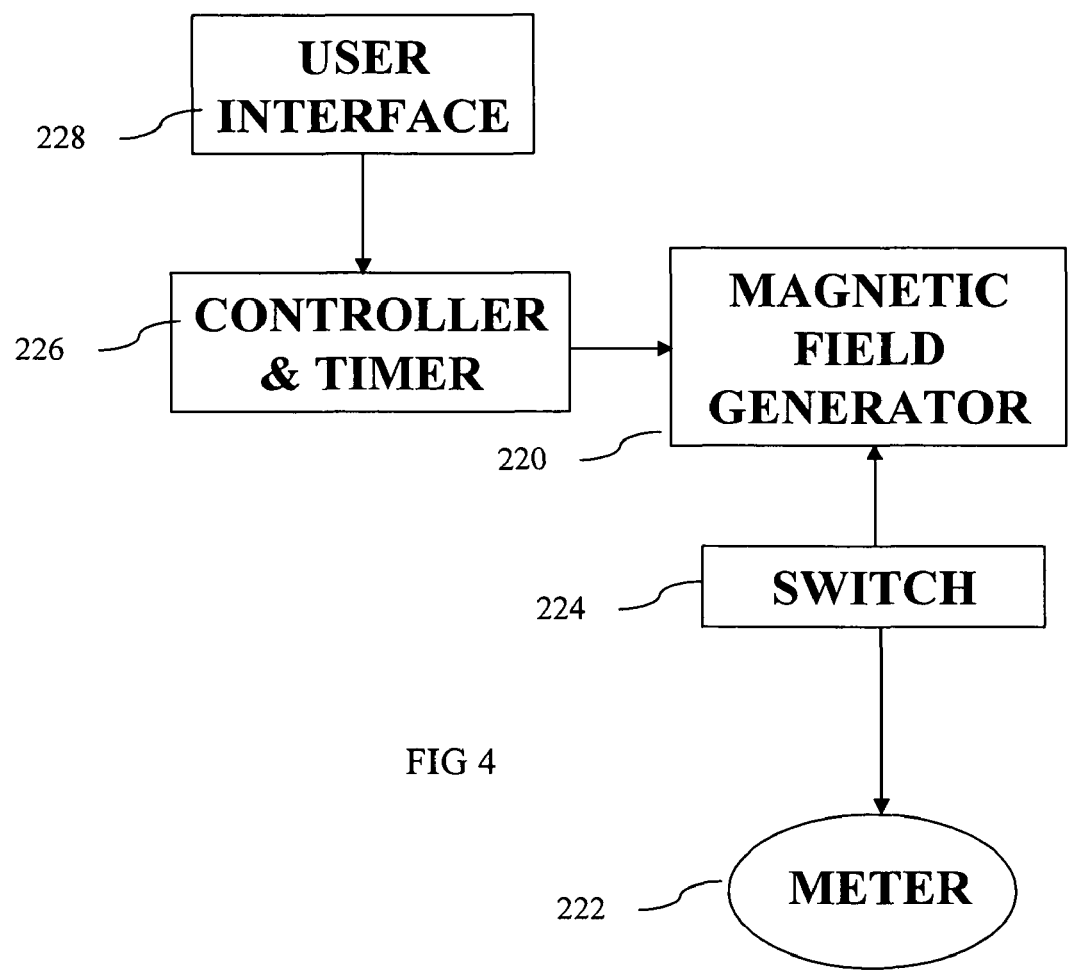
FIG. 4 illustrates a circuit of one aspect of a magnetizing device.

FIG. 4 illustrates a circuit diagram of the magnetizing device 200 of FIG. 2. The magnetic field generator 220 and the meter 222 are controlled by a switching circuit 224 in a manner already described. A controller and timer circuit 226 that is controlled by a user interface 228 controls the operation of the magnetic field generator 220. The controller and timer circuit 226 includes the regulator that regulates the strength of the output of the magnetic field generator 220. The regulator is controlled by a switch provided in the user interface 228. The controller and timer circuit 226 also includes a timer that controls the amount of time that the magnetic field is generated by the magnetic field generator 220. The timer is controlled by an interface provided in the user interface 228.

Figure 5:
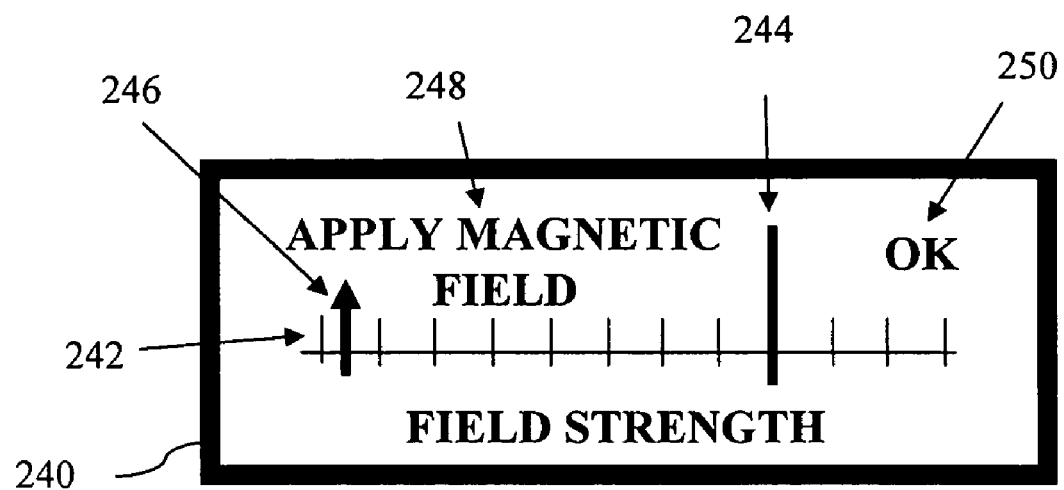
FIG. 5 shows a display on a meter on the magnetizing device.

The meter 203 preferably has a display 240, shown in FIG. 5. A scale 242 is provided on the display 240. A threshold indicator 244 is provided on the scale. The position of the threshold indicator 244 on the scale 242 is preferably adjustable. A marker 246 is provided on the scale, the position of the marker 246 indicating the measured magnetic field strength. Two labels are preferably provided on the display 240. One label 248 is below the threshold indicator 244 and indicates that if the magnetic field measured on an object is less than the level of the threshold indicator 244, then an additional dosage of magnetic field should be applied to the object. The second label 250 is above the threshold indicator 244 and it indicates that no additional dosage of magnetic field should be applied.

Figure 6:
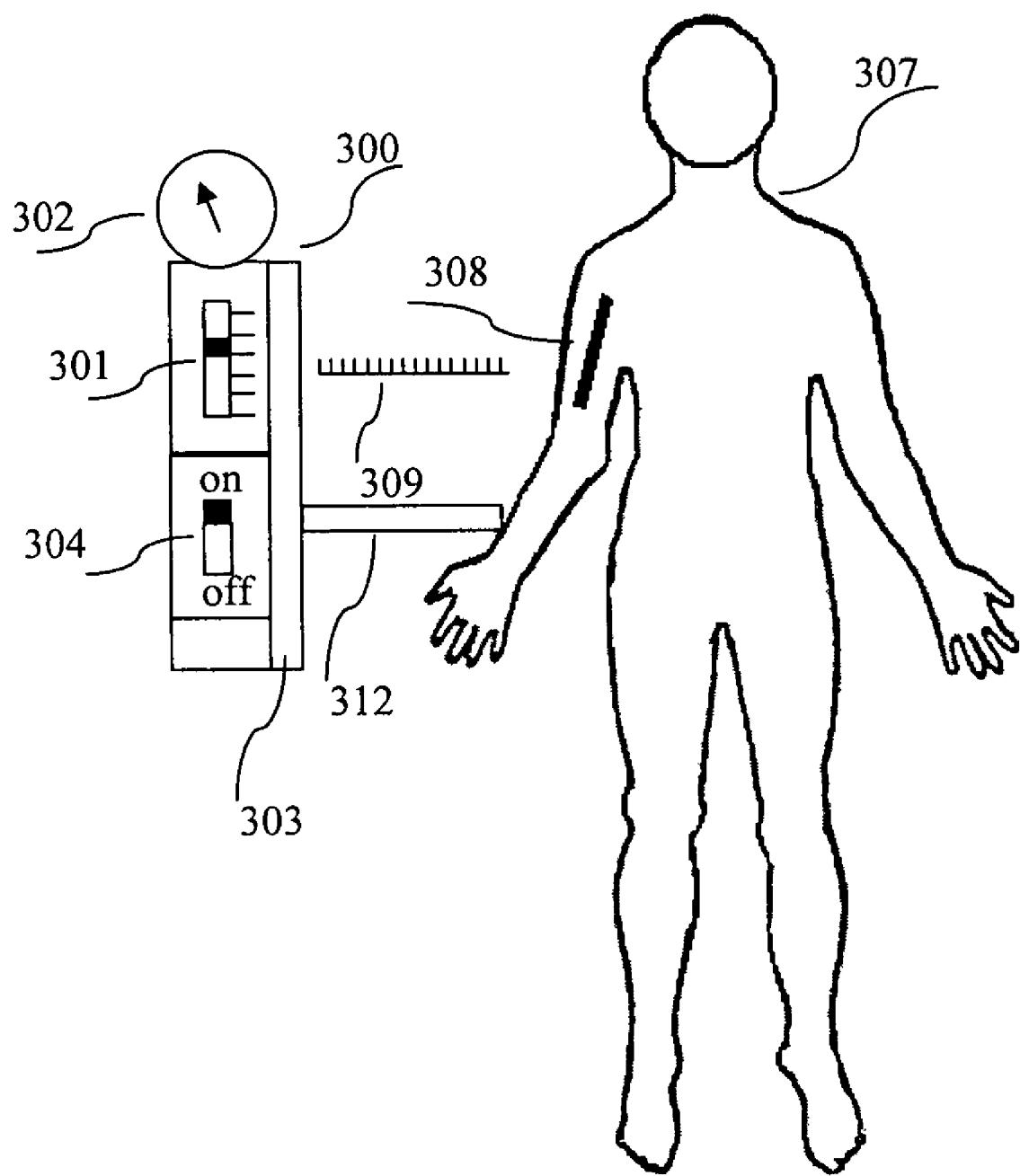
FIG. 6 illustrates the use of one aspect of the present invention.

As an illustrative example, FIG. 6 shows how a magnetizing device 300 can be used on a patient 307 to magnetize an object 308 in the patient 307. The magnetizing device 300 is positioned in a known position by using, for example, a measuring tape 309. This allows the object 308 to be magnetized at different times with an identical magnetic field strength. The magnetizer has initially its switch 304 in the off position so that no magnetic field is generated. The regulator 301 is set in the desired position. If a timer is to be used, the length of time is selected through a user interface. The magnetizing device 300 is put in the desired position, if needed by using a device like the measuring tape 309. The switch 304 is put in the ON position. One can check on meter 302 if the magnetic field is of desired strength and if needed adjust the strength by regulator 301. Then, the magnetic field generator 303 is disabled by a switch, and, the magnetic field strength emanating from the object 307 can be measured with the meter 302. For accurate readings, the device 300 is put into a known position with, for example, a tape measure. It is noted, however, that the use of a tape measure is entirely optional. Further, a measuring component 312 that extends from the device 300 can be provided to accurately measure the distance of the device 300 from a body 307.

It is known that the strength of a magnetic field that is measured on a distance from a magnetizer is not identical to the strength of the magnetic field close to the magnetizer. Also the magnetic field induced in an object or in micro encapsulated ferrous substances in a body may be different from the strength of a field generated by the magnetizer at the position of the object or the micro encapsulated substance. Further more it is known that materials may demagnetize over time and lose in strength of magnetic field over time. It is important to be able to measure, control and replace the fading magnetic field as needed. It is an aspect of the present invention to provide a meter that can measure the strength of the magnetic field generated by objects or particles in the body. In this case, the meter is used in conjunction with the magnetic field system, but does not necessarily have to be connected to the magnetizer. Thus, the magnetic field generator and the meter can be provided in a kit as separate components. It may be desirable to measure or to monitor the strength of the magnetic field of objects and particles in patients away from the location of the magnetizer, for instance at home. Such meters can be inexpensive, simple and easy to use. They can for instance use available Hall Effect based magnetic field instruments.

The meter can also be used to measure the output of the magnetic field generator. The strength of the magnetic field measured from the generator may be significantly different than the strength of the magnetic field generated by an object in the body. Thus, the meter can have two selectable scales. One scale is selected when measuring an object and the second scale is selected if measuring the output of the magnetic field generator.

Figure 7:
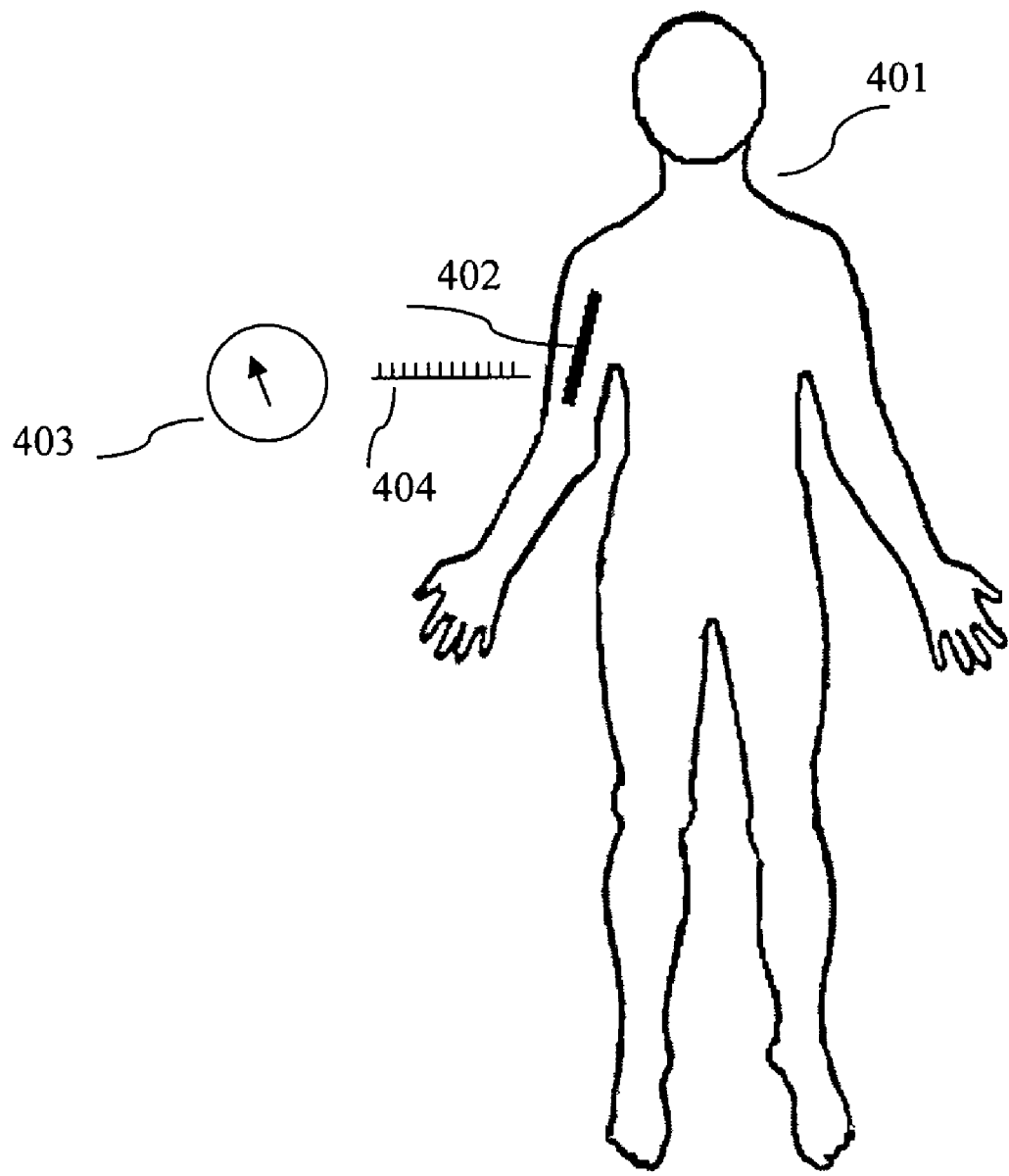
FIG. 7 illustrates the use of a magnetic field meter.

FIG. 7 shows how a meter can be used. A patient 401 has an object 402 that has been magnetized to a desired strength of magnetic field. The strength of the magnetic field has been measured directly after magnetization by a magnetic field meter 403. The position of this meter relative to the position of the magnetized object 402 in the patient has been recorded. It may have been measured by a measuring tape 404. It may also have been placed at a known position at the skin of the patient. At different times the magnetic field meter 403 or its equivalent may be used in the identical position relative to the magnetized object 402 to measure the magnetic field strength. If the strength of the field has faded below a certain level, the patient may receive a treatment to recharge the object according to the method provided by the present invention.

Figure 8:
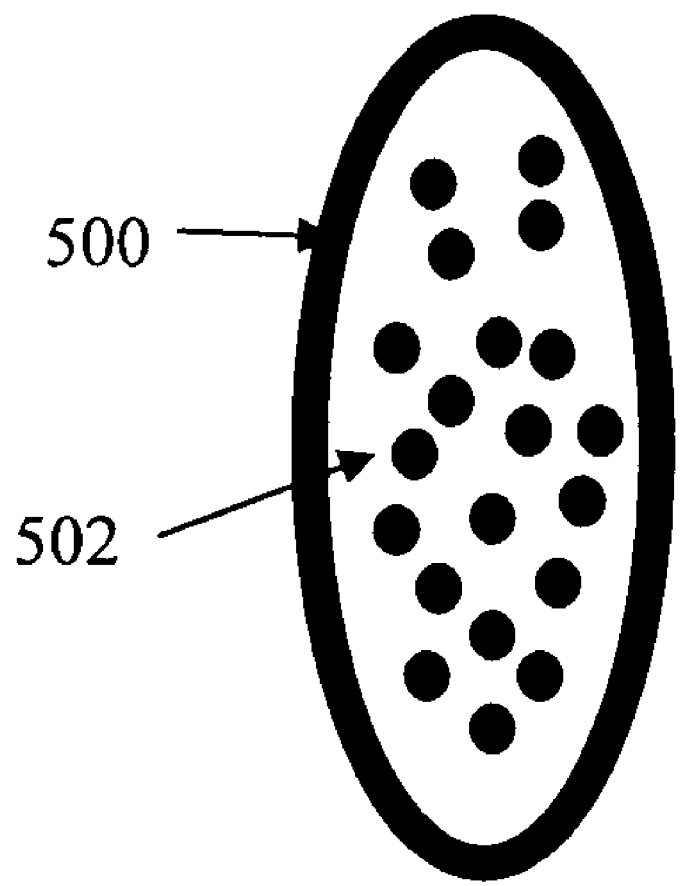
FIG. 8 illustrates a pill in accordance with one aspect of the present invention.

FIG. 8 illustrates a pill 500 useful various aspects of the present invention. The pill 500 has metallic particles 502, such as ferrous particles, that are microencapsulated or encapsulated in some form. The magnetizing devices of the present invention are used to magnetize the pill 500 and then the pill 500 is swallowed. A meter can be used to measure the magnetic field emanating from the pill 500 before it is swallowed or after it is swallowed. Such a magnetized pill can provide therapeutic magnetic field therapy to digestive systems in treatment of such situations as irritable bowel syndrome.

Figure 9:
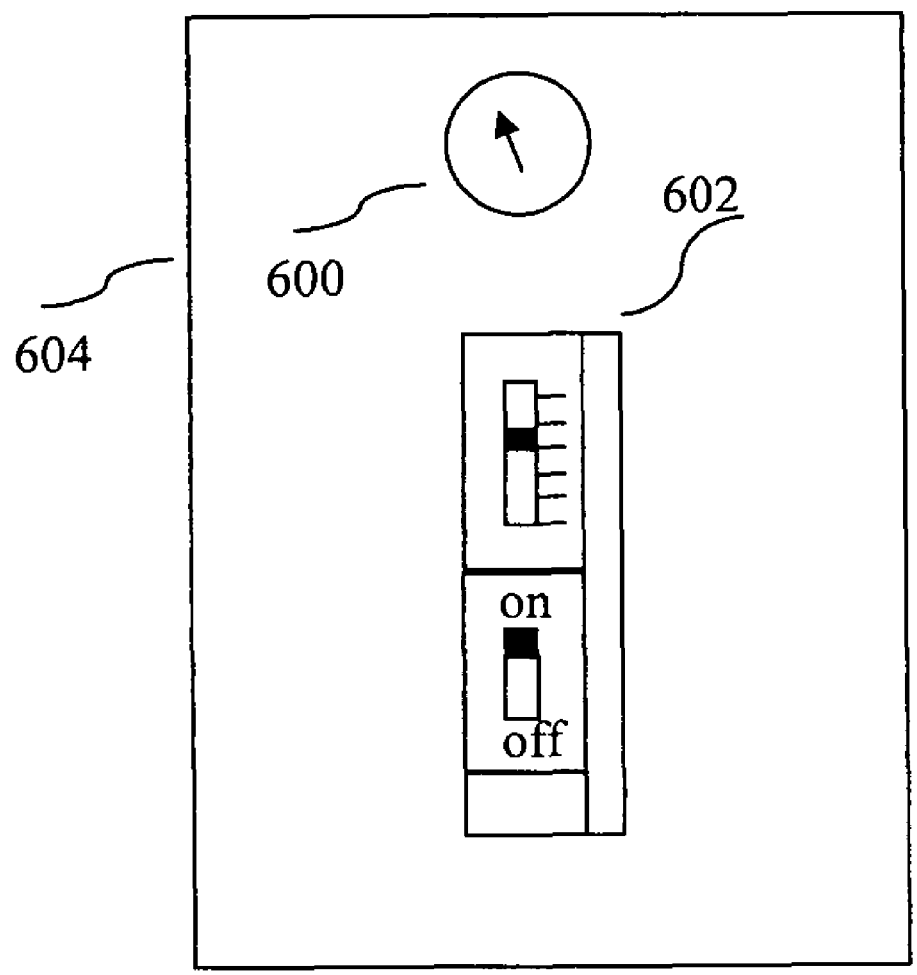
FIG. 9 illustrates a kit in accordance with one aspect of the present invention.

FIG. 9 illustrates a kit in accordance with one aspect of the present invention. The kit includes a magnetic field generator 602 and a meter 600, both of which are enclosed in a single package 604.

The methods and apparatus of the present invention are useful in promoting the general wellness of persons. It is also useful in promoting the general wellness of animals.

The present invention is further useful in creating repeatable and measurable therapeutic magnetic treatments. It is also important in clinical studies to correlate the healing of the patient and pain relief experiences with the intensity of the magnetism to develop the optimum treatment for each stage. By combining the machine that generates the magnetism with a reader that measures the magnetism of the metal part or micro encapsulated product the present invention is of significant medical use in the control of pain and in the healing of certain types of medical problems.

Modifications of this invention will be readily apparent to those skilled in the art and it is intended that the invention be not limited by the embodiments disclosed herein but that the scope of the invention be defined by the appended claims.

I claim:

1. A method of providing a therapeutic magnetic field comprising:
   applying a magnetic field generated by a magnetic field generator to a patient so as to induce a magnetic field in a magnetizable object; and
   measuring the patient with a meter, while the magnetic field from the magnetic field generator is disabled, to determine magnetic field strength of the magnetic field emanating from the object.

2. The method of claim 1, further comprising indicating if the magnetic field strength is below a threshold.

3. The method of claim 2, further comprising after indicating the magnetic field strength is below a threshold, applying the magnetic field generated by the magnetic field generator again to the patient to recharge the magnetic field in the magnetizable object.

4. The method of claim 1, wherein the magnetizable object comprises a plurality of magnetizable particles on the skin of the patient.

5. The method of claim 1, further comprising spreading a composition including a plurality of the magnetizable objects on the skin of the patient.

6. The method of claim 1, further comprising measuring position of the meter relative to the patient to establish a known position, wherein measuring the patient with the meter is conducted with the meter at the known position.

7. The method of claim 6, wherein measuring position is performed by a measuring component extending from the meter.

8. The method of claim 1, wherein measuring the patient with the meter is conducted with the meter against the skin of the patient.

9. The method of claim 1, wherein the object is a metal orthopedic device.

10. The method of claim 1, wherein applying the magnetic field comprises generating the magnetic field for a preselected time and then disabling the magnetic field.

11. A method of providing a therapeutic magnetic field comprising:
    spreading a composition including a plurality of the magnetizable objects on the skin of a patient;
    applying a magnetic field generated by a magnetic field generator to the patient so as to induce a magnetic field in the magnetizable objects; and
    measuring the patient with a meter to determine magnetic field strength of the magnetic field emanating from the magnetizable objects, wherein measuring the patient is performed when the magnetic field generated by the magnetic field generator is disabled.

12. The method of claim 11, wherein the composition comprises a cream.

13. The method of claim 11, wherein the composition comprises a lotion.

14. The method of claim 11, wherein the magnetizable objects comprise ferrous material.

15. The method of claim 11, further comprising indicating if the magnetic field strength is below a threshold.

16. The method of claim 15, further comprising after indicating the magnetic field strength is below a threshold, applying the magnetic field generated by the magnetic field generator again to the patient to recharge the magnetic field in the magnetizable objects.

17. The method of claim 11, further comprising measuring position of the meter relative to the patient to establish a known position, wherein measuring the patient with the meter is conducted with the meter at the known position.

18. The method of claim 17, wherein measuring position is performed by a measuring component extending from the meter.

19. The method of claim 11, wherein measuring the patient with the meter is conducted with the meter against the skin of the patient.

20. The method of claim 11, wherein applying the magnetic field comprises generating the magnetic field for a preselected time and then disabling the magnetic field.

21. A method of providing a therapeutic magnetic field comprising:
    spreading a composition including a plurality of the magnetizable objects on the skin of a patient;
    applying a magnetic field generated by a magnetic field generator to the patient so as to induce a magnetic field in the magnetizable objects;
    measuring the patient with a meter to determine magnetic field strength of the magnetic field emanating from the magnetizable objects; and
    measuring position of the meter relative to the patient to establish a known position, wherein measuring the patient with the meter is conducted with the meter at the known position.

22. The method of claim 21, further comprising indicating if the magnetic field strength is below a threshold.

23. The method of claim 22, further comprising after indicating the magnetic field strength is below a threshold, applying the magnetic field generated by the magnetic field generator again to the patient to recharge the magnetic field in the magnetizable objects.

24. The method of claim 21, wherein measuring position is performed by a measuring component extending from the meter.

25. The method of claim 21, wherein applying the magnetic field comprises generating the magnetic field for a preselected time and then disabling the magnetic field.

* * * * *